United States Patent
Kearns et al.

(10) Patent No.: US 7,552,027 B2
(45) Date of Patent: Jun. 23, 2009

(54) METHOD AND SYSTEM FOR QUANTIFYING DAMAGE IN A STRUCTURE

(75) Inventors: Justin D. Kearns, Seattle, WA (US); Jeong-Beom Ihn, Bellevue, WA (US)

(73) Assignee: The Boeing Company, Chicago, IL (US)

(*) Notice: Subject to any disclaimer, the term of this patent is extended or adjusted under 35 U.S.C. 154(b) by 81 days.

(21) Appl. No.: 11/867,210

(22) Filed: Oct. 4, 2007

(65) Prior Publication Data
US 2009/0093999 A1    Apr. 9, 2009

(51) Int. Cl.
G06F 19/00 (2006.01)
(52) U.S. Cl. .......................... 702/182; 700/9
(58) Field of Classification Search ............... 702/132, 702/182, 181, 183, 184, 185, 188, 33–36, 702/42, 43, 58, 59; 700/9, 21, 110
See application file for complete search history.

(56) References Cited

U.S. PATENT DOCUMENTS

| | | | |
|---|---|---|---|
| 5,774,376 A | | 6/1998 | Manning |
| 6,006,163 A | * | 12/1999 | Lichtenwalner et al. ....... 702/36 |
| 2006/0004499 A1 | | 1/2006 | Trego et al. |
| 2006/0234055 A1 | * | 10/2006 | Wu et al. .................... 428/408 |
| 2006/0243180 A1 | * | 11/2006 | Sundermeyer et al. . 112/470.06 |

FOREIGN PATENT DOCUMENTS

WO    02062206 A3    8/2002

OTHER PUBLICATIONS

X. Zhao, H. Gao, G. Zhang, B. Ayhan, F. Yan, C. Kwan and J. Rose; "Active Health Monitoring of an Aircraft Wing with Embedded Piezoelectric Sensor/Actuator Network: I. Defect Detection, Localization and Growth Monitoring"; Smart Materials and Structures; IOP Publishing, Ltd., published Jun. 29, 2007.
UK Intellectual Property Office Search Report; Application No. GB0818264.4; Jan. 6, 2009.

* cited by examiner

*Primary Examiner*—Edward Raymond
(74) *Attorney, Agent, or Firm*—Law Office of Donald D. Mondul

(57) ABSTRACT

A method for quantifying damage in a test structure having a plurality of transducer units coupled to at least one portion of the test structure includes: (a) training an evaluating algorithmic system coupled with the transducer units to establish a trained algorithmic system able to recognize a plurality of characteristics of signals traversing a plurality of paths through a training structure substantially similar to the test structure after the training structure is damaged. Each path is situated between a respective pair of transducer units coupled to the training structure; the plurality of characteristics relates each path to a plurality of physical aspects of the damage. A trained algorithmic system is employed to recognize the plurality of characteristics of signals traversing paths in the test structure to effect the quantifying. The plurality of physical aspects includes less than ten physical aspects.

20 Claims, 5 Drawing Sheets

METHOD AND SYSTEM FOR QUANTIFYING DAMAGE IN A STRUCTURE

FIELD OF THE DISCLOSURE

The disclosure is directed to Structural Health Monitoring (SHM) methods and systems, and especially to methods and systems for quantifying damage in structures.

BACKGROUND

A Structural Health Monitoring (SHM) system may improve unscheduled and scheduled maintenance operations. An SHM system may advantageously quickly identify occurrence of damage, determine damage location and size, and schedule an appropriate remedial maintenance action. Such an SHM system may reduce maintenance costs.

An SHM system employed with an aircraft, by way of example and not by way of limitation near the fuselage cargo door of an aircraft where baggage handlers may collide with and cause impact damage to the airplane fuselage, may reduce aircraft schedule cancellations and delays. An SHM system may be particularly advantageous when employed in connection with laminated structures to identify, locate and characterize delamination damage.

Large masses of data may be processed in an SHM system, in part because little is known regarding sensitivity of various parameters vis-à-vis damage characteristics. One resulting method may have been a tendency to process a large number of parameters to avoid missing something important. As a result of large volumes of data handling, an SHM system may yield computationally intensive and impractical methods, inaccurate damage detection results, false positives or false negatives because of data confusion.

There is a need for a method and system for quantifying damage in a structure that may be efficient and timely in operation.

There is a need for a method and system for quantifying damage in a structure that may employ parameters sensitive to identification and quantification of damage characteristics.

SUMMARY

A method for quantifying damage in a test structure having a plurality of transducer units coupled to at least one portion of the test structure includes: (a) Training an evaluating algorithmic system coupled with the transducer units to establish a trained algorithmic system able to recognize a plurality of characteristics of signals traversing a plurality of paths through a training structure substantially similar to the test structure after the training structure is damaged. Each path is situated between a respective pair of transducer units coupled to the training structure; the plurality of characteristics relates each path to a plurality of physical aspects of the damage. (b) Employing a trained algorithmic system to recognize the plurality of characteristics of signals traversing paths in the test structure to effect the quantifying. The plurality of physical aspects includes less than ten physical aspects.

A system for evaluating structural changes in a test piece having damage includes: (a) a training piece substantially similar to the test piece; (b) a training algorithmic system coupled with the training piece; (c) a plurality of training transducer elements coupled with the training piece and with the training algorithmic system; the plurality of training transducer elements being exercised by transmitting a plurality of training signals among the plurality of training transducer elements after imposing damage to the training piece; the training algorithmic system processing information in the training signals relating to predetermined parameters relating to the evaluating; adjusting weighted factors used by the training algorithmic system to reduce errors between results from the training algorithmic system and the predetermined parameters; the transmitting of training signals and adjusting of weighted factors continuing until the errors are reduced to within predetermined limits; the predetermined parameters relating to a plurality of physical aspects of the damage; and (d) a trained algorithmic system substantially similar to the training algorithmic system coupled with the test piece to process a plurality of test signals similar to the training signals to effect the evaluating; the plurality of physical aspects being less than ten physical aspects of the damage.

It is, therefore, a feature of embodiments of the disclosure to provide a method and system for quantifying damage in a structure that may be efficient and timely in operation.

It is another feature of embodiments of the disclosure to provide a method and system for quantifying damage in a structure that may employ parameters sensitive to identification and quantification of damage characteristics.

Further features of embodiments of the present disclosure will be apparent from the following specification and claims when considered in connection with the accompanying drawings, in which like elements are labeled using like reference numerals in the various figures, illustrating embodiments of the disclosure.

DETAILED DESCRIPTION

Figure 1:
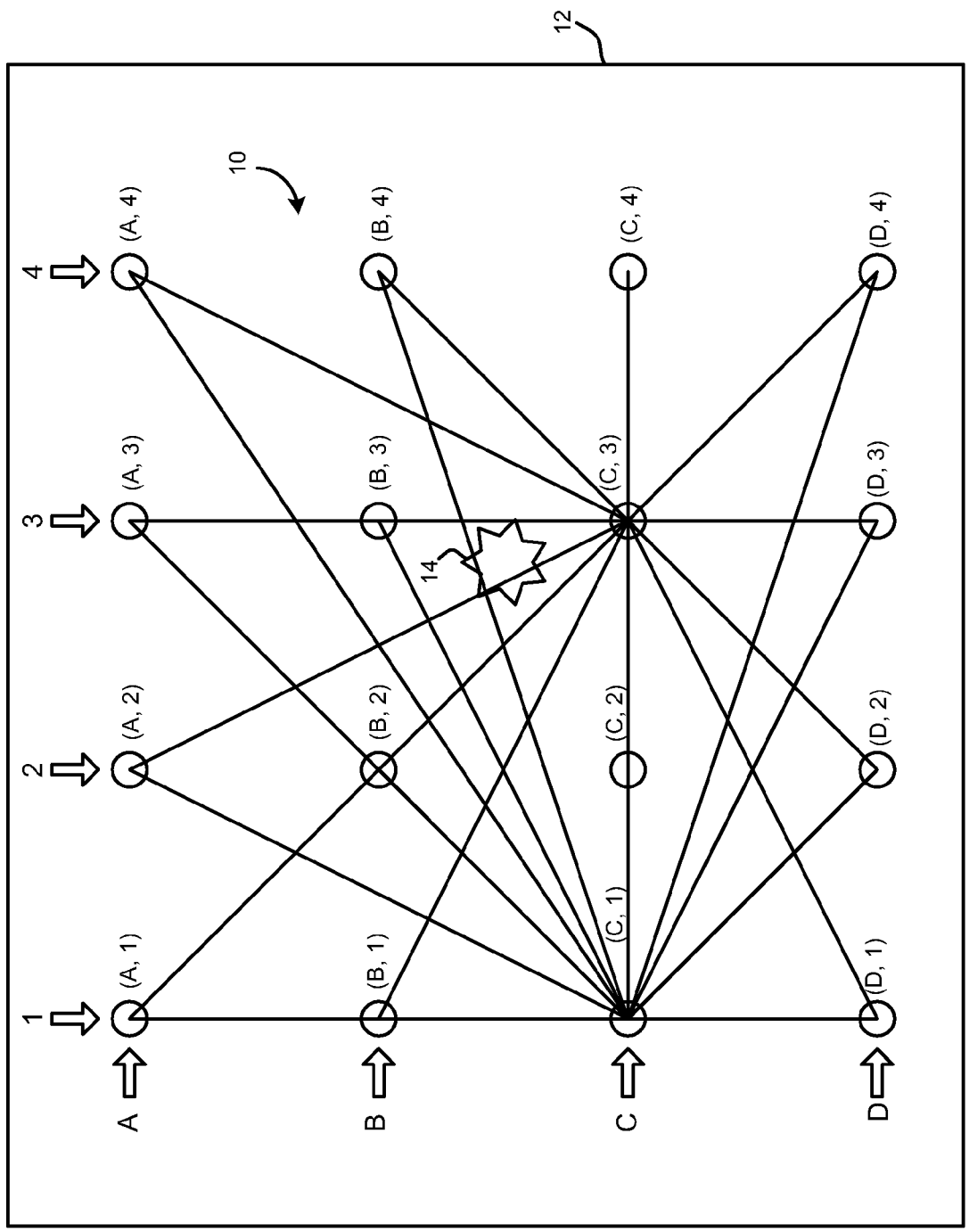
FIG. 1 is a schematic illustration of a transducer array useful in effecting embodiments of the present disclosure.

FIG. 1 is a schematic illustration of a transducer array useful in effecting embodiments of the present disclosure. In FIG. 1, an array of transducer elements 10 may be affixed or coupled to a structure 12. Array 10 may present an arrangement of transducer elements in any pattern. An exemplary preferred pattern may be a rectangular grid having rows A, B, C, D and columns 1, 2, 3, 4, as illustrated in FIG. 1. Using such an arrangement, individual transducer elements may be identified using (row, column) coordinates. Thus, column 1 may contain a transducer element (A,1) in row A, a transducer element (B,1) in row B, a transducer element (C, 1) in row C and a transducer element (D,1) in row D. Column 2 may contain a transducer element (A,2) in row A, a transducer element (B,2) in row B, a transducer element (C,2) in row C and a transducer element (D,2) in row D. Column 3 may contain a transducer element (A,3) in row A, a transducer element (B,3) in row B, a transducer element (C,3) in row C and a transducer element (D,3) in row D. Column 4 may contain a transducer element (A,4) in row A, a transducer element (B,4) in row B, a transducer element (C,4) in row C and a transducer element (D,4) in row D. Array 10 is exemplary only. An array of transducer elements may contain a greater or lesser number of transducer elements if desired.

During training or evaluation of damage operations each respective transducer element may be excited to transmit a signal which may be received by some or all of the remaining non-transmitting transducer elements. A signal path may be thereby established between each transmitting-receiving transducer-pair. One may excite each transducer individually for presenting a respective signal for receiving by non-transmitting transducer elements to establish a plurality of signal paths traversing the array 10 of transducer elements.

One may observe that there may be presented a total of 240 (16×15) signal paths in array 10 after all 16 transducer elements have had a turn at transmitting. In order to avoid a cluttered and confusing presentation, FIG. 1 illustrates only two representative transmitting transducer elements (C,1), (C,3). One of transducer elements (C,1), (C,3) may transmit first along a first set of 15 signal paths for receiving by other then-non-transmitting transducer elements in array 10. Subsequently, an other transducer of transducer elements (C,1), (C,3) may transmit along a second set of 15 signal paths for receiving by other then-non-transmitting transducer elements in array 10.

A damage locus 14 is also indicated in FIG. 1. One may also observe that selected signal paths presented in array 10 may pass near damage locus 14 or traverse damage locus 14. Structural changes may occur in structure 12 as a result of damage situated at damage locus 14, and such structural changes may alter selected characteristics of signals traversing signal paths in the vicinity of damage locus 14 or traversing damage locus 14.

An algorithmic system may be trained to associate observed anomalies in signals received by receiving transducer elements with at least one training structure having selected physical manifestations of damage. The training process may involve transmitting signals through structure 12 from all transducer elements in array 10 and recording signal characteristics of signals received by receiving transducer elements when there is damage to structure 12. The training algorithmic system may process information in the training signals relating to predetermined parameters relating to a plurality of measured aspects of the damage. Weighted factors used by the training algorithmic system may be adjusted to reduce errors between results from the training algorithmic system and the measured aspects of the damage. The process of parameter measuring and weighting factor adjustment may be repeated until the errors between results from the training algorithmic system and the measured aspects of the damage are within predetermined limits.

Such measuring of predetermined characteristics of the imposed damage may permit recognition of an association with the measured parameters and characteristics of received signals traversing selected signal paths. Measurement of characteristics relating to a damage locus may be effected using one or more known measurement techniques such as, by way of example and not by way of limitation, physical measurement using calipers, dividers, distance scales and similar instruments; x-ray measurements, ultrasonic measurements and other known measurement techniques.

A training operation may further involve repeating the above-described process using a plurality of training pieces in order to refine associations observed between measured parameters of damage loci and weighted factors employed by a training algorithmic system.

Once the algorithmic system is trained, it may be substantially copied to present a trained algorithmic system that may be employed to evaluate a test piece. Signals may be transmitted through the test piece substantially as signals were transmitted through one or more training pieces and characteristics of signals received by receiving transducer elements may be evaluated. The nature of the observed signals may be employed to estimate predetermined aspects of the damage based upon the correlations between signal changes and damage parameters "learned" by the algorithmic system during the training operation.

One example of an algorithmic system suitable for use in evaluating signals from array 10, such as by way of example and not by way of limitation in a Structural Health Monitoring (SHM) system, may be a nonlinear statistical data modeling and learned classification method, such as an artificial neural network. By way of simplifying this description and not by way of limitation, this description shall describe embodiments of the disclosure employing an artificial neural network. In order for a neural network to generalize a data space and accurately perform, it may be preferred that a small number of inputs be included in each input set. Too large a number of inputs may cause a neural network to be time inefficient and the network may require an unrealistic number of data sets, thereby rendering the algorithm incapable of accurately predicting damage of a large range of possible sizes.

Figure 2:
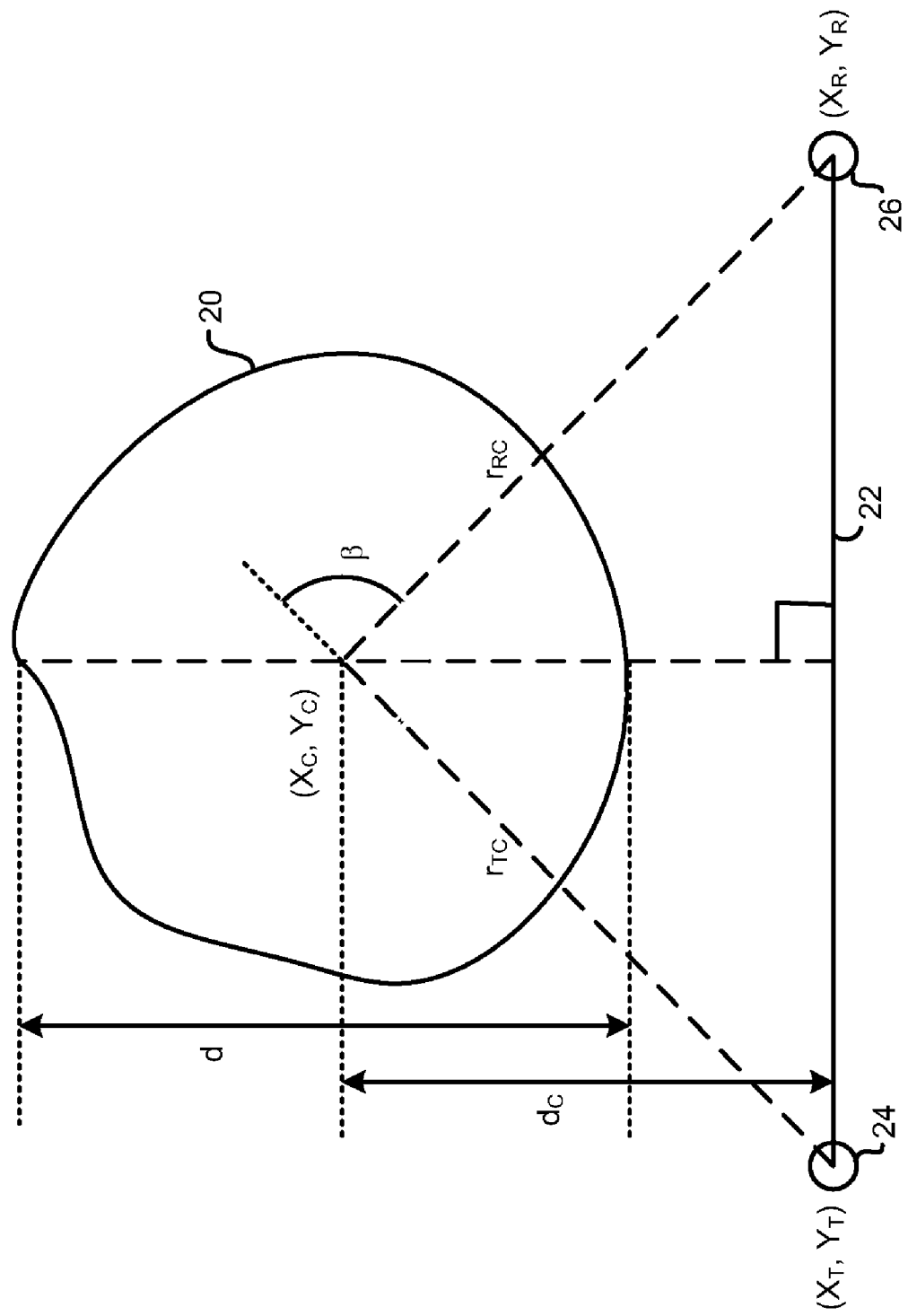
FIG. 2 is a schematic illustration of representative parameters useful in quantifying damage in a structure.

FIG. 2 is a schematic illustration of representative parameters useful in quantifying damage in a structure. In FIG. 2, a damage locus 20 may be situated with a signal path 22 established between a transmitting transducer element 24 located at a position $(X_T, Y_T)$ and a receiving transducer element 26 located at a position $(X_R, Y_R)$. By way of example and not by way of limitation, transmitting transducer element 24 at position $(X_T, Y_T)$ may be transducer element (C, 3) in FIG. 1; and receiving transducer element 26 at position $(X_R, Y_R)$ may be transducer element (B, 3) in FIG. 1.

One parameter that may be associated with damage locus 20 may be a Damage Index (DI). A DI may be calculated in association with signal path 22. DIs are known in the art of Structural Health Monitoring (SHM) systems, and may indicate a measure of the difference between pre-damage and post-damage signals. A DI may be calculated using any one or more of a number of varied methods known to those skilled in the art of SHM systems.

Another parameter that may be associated with damage locus 20 may be a distance $r_{TC}$, the linear distance from transmitting transducer element 24 to center of damage locus 20 located at coordinates $(X_C, Y_C)$.

Still another parameter that may be associated with damage locus 20 may be a distance $r_{RC}$, the linear distance from receiving transducer element 26 to center of damage locus 20 located at coordinates $(X_C, Y_C)$.

Yet another parameter that may be associated with damage locus 20 may be a perpendicular distance $d_C$ from signal path 22 to center of damage locus 20 located at coordinates $(X_C, Y_C)$.

Another parameter that may be associated with damage locus 20 may be a scatter angle $\beta$, the complementary angle of the intersection of radii $r_{TC}$, $r_{RC}$.

The inventors have found by experimentation that the above five parameters—DI, $r_{TC}$, $r_{RC}$, $d_C$, $\beta$—are sensitive to employing an artificial neural network for determining local diameter d of damage locus 20 measured on the perpendicular from signal path 22 through center of damage locus 20 located at coordinates $(X_C, Y_C)$.

Figure 3:
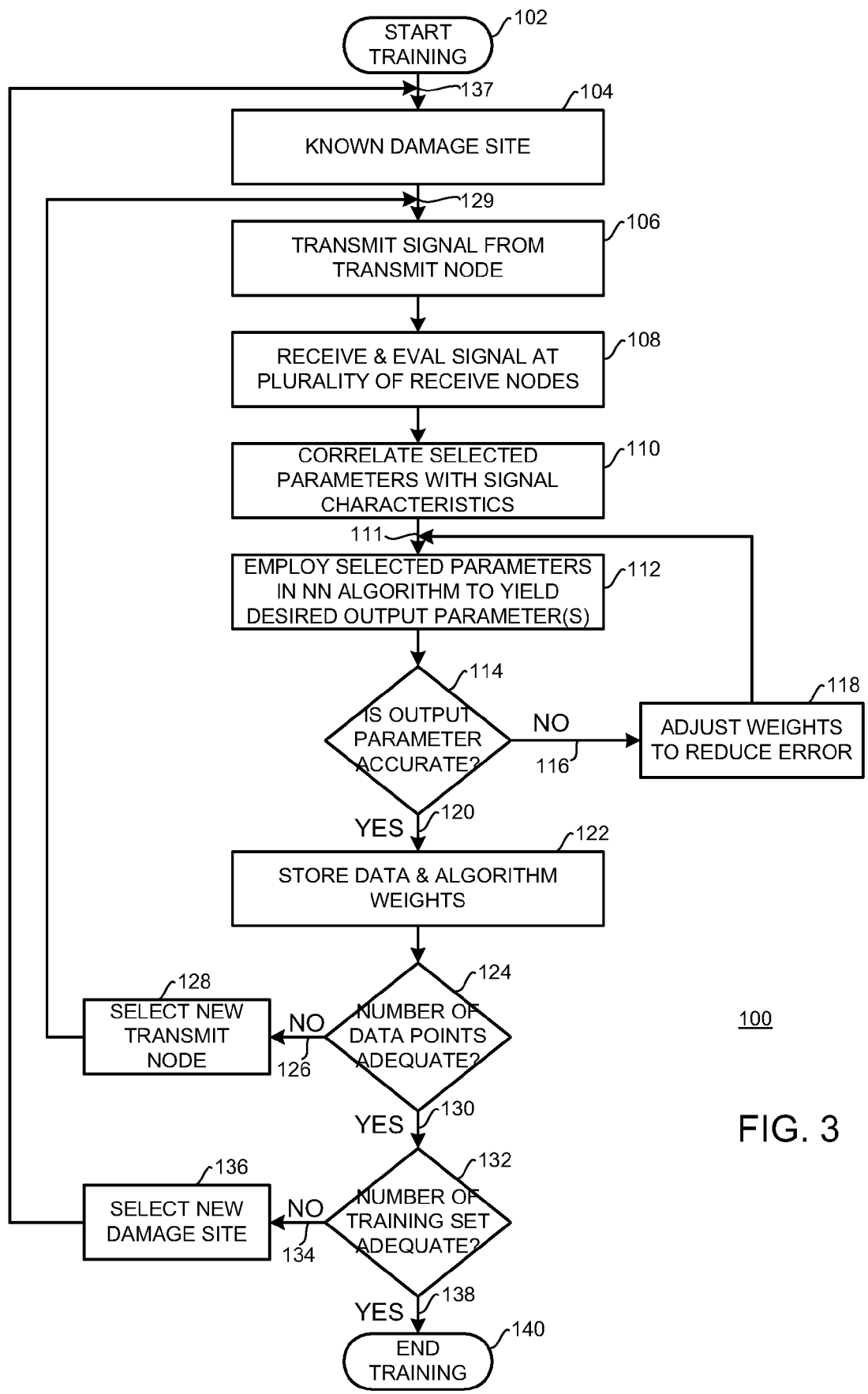
FIG. 3 is a flow chart illustrating steps involved in training a system for quantifying damage in a structure.

FIG. 3 is a flow chart illustrating steps involved in training a system for quantifying damage in a structure. In FIG. 3, a method 100 for training a system for quantifying damage in a structure may begin at a START TRAINING locus 102. By way of example and not by way of limitation, method 100 may illustrate steps for training a neural network algorithmic system, or another type of classification routine, for use in an SHM system to qualify or characterize damage in a structure.

Method 100 may continue with establishing a known damage site in the structure, as indicated by a block 104. Method 100 may continue by transmitting a signal from a transmit node or transmitting transducer element, as indicated by a block 106.

Method 100 may continue with receiving and evaluating signals at a plurality of receiving nodes or receiving transducer elements, as indicated by a block 108.

Method 100 may continue with correlating selected parameters with characteristics of the received signals, as indicated by a block 110. The selected parameters may be associated with a plurality of physical aspects of the damage.

Method 100 may continue with employing the selected parameters in a training algorithmic system such as, by way of example and not by way of limitation, an artificial neural network (NN) system to yield desired output parameters associated with the damage, as indicated by a block 112.

Method 100 may continue by posing a query whether the output parameters generated in association with the step represented by block 112 are accurate to within a predetermined limit, as indicated by a query block 114. If the output parameters generated in association with the step represented by block 112 are not accurate to within a predetermined limit, method 100 may proceed from query block 114 via a NO response line 116 and weighted factors used by the training algorithmic system to reduce errors between results from the training algorithmic system and the predetermined parameters may be adjusted to reduce the errors, as indicated by a block 118. Method 100 may proceed from block 118 to a locus 111 and method 100 thereafter repeat steps indicated by blocks 112, 114.

If the output parameters generated in association with the step represented by block 112 are accurate to within a predetermined limit, method 100 may proceed from query block 114 via a YES response line 120 and may store data and algorithm weights associated with the received signals, as indicated by a block 122.

Method 100 may continue by posing a query whether the number of data points stored (block 122) is adequate to evaluate structures to acceptable accuracy, as indicated by a query block 124. If the number of data points stored is not adequate to evaluate structures to acceptable accuracy, method 100 may proceed from query block 124 via a NO response line 126 and a new transmit node or transducer element is selected, as indicated by a block 128. Method 100 may proceed from block 128 to a locus 129 and method 100 may thereafter repeat steps indicated by blocks 106, 108, 110, 112, 114, 118, 122, 124.

If the number of data points stored is adequate to evaluate structures to acceptable accuracy, method 100 may proceed from query block 124 via a YES response line 130 and may pose a query whether the number of training sets of data is adequate to evaluate structures, as indicated by a query block 132. If the number of training sets of data is not adequate to evaluate structures, method 100 may proceed from query block 132 via a NO response line 134 and a new damage site is selected, as indicated by a block 136. The new damage site may be located in a new training structure. Method 100 may proceed from block 136 to a locus 137 and method 100 may thereafter repeat steps indicated by blocks 104, 106, 108, 110, 112, 114, 118, 122, 124.

If the number of training sets of data is adequate to evaluate structures, method 100 may proceed from query block 132 via a YES response line 138 and method 100 may terminate, as indicated by an END TRAINING locus 140.

Figure 4:
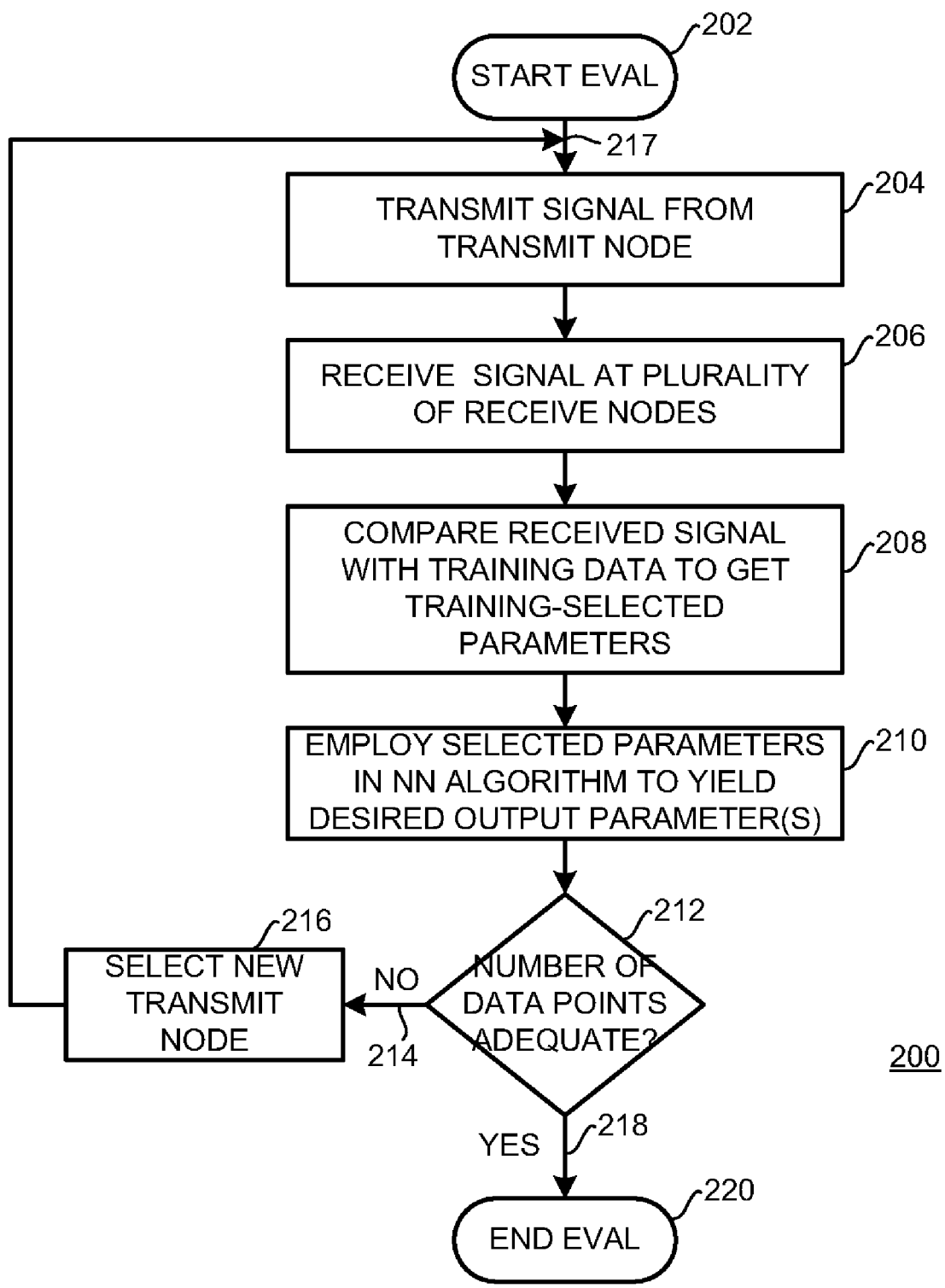
FIG. 4 is a flow chart illustrating steps involved in quantifying damage in a structure.

FIG. 4 is a flow chart illustrating steps involved in quantifying damage in a structure. In FIG. 4, a method 200 for quantifying damage in a structure may begin at a START EVAL locus 202. Method 200 may continue with transmitting a signal from a transmit node or transducer element, as indicated by a block 204.

Method 200 may continue with receiving the signal at a plurality of receive nodes or receiving transducer elements, as indicated by a block 206.

Method 200 may continue with comparing the received signals with training data to obtain training-selected parameters, as indicated by a block 208. The training data may have been stored during a training operation such as indicated at block 122; FIG. 3.

Method 200 may continue with employing selected parameters in an algorithmic system to yield desired output parameters, as indicated by a block 210. The algorithmic system may be embodied in an artificial neural network (NN) algorithm system.

Method 200 may continue by posing a query whether the number of data points is adequate to effect an evaluation with acceptable accuracy, as indicated by a query block 212. If the number of data points is not adequate to effect an evaluation with acceptable accuracy method 200 may proceed from query block 212 via a NO response line 214 and a new transmit node or transducer element may be selected, as indicated by a block 216. Method 200 may proceed to a locus 217 and method 200 may thereafter repeat steps indicated by blocks 204, 206, 208, 210, 212.

If the number of data points is adequate to effect an evaluation with acceptable accuracy method 200 may proceed from query block 212 via a YES response line 218 and method 200 may terminate, as indicated by an END EVAL locus 220.

Figure 5:
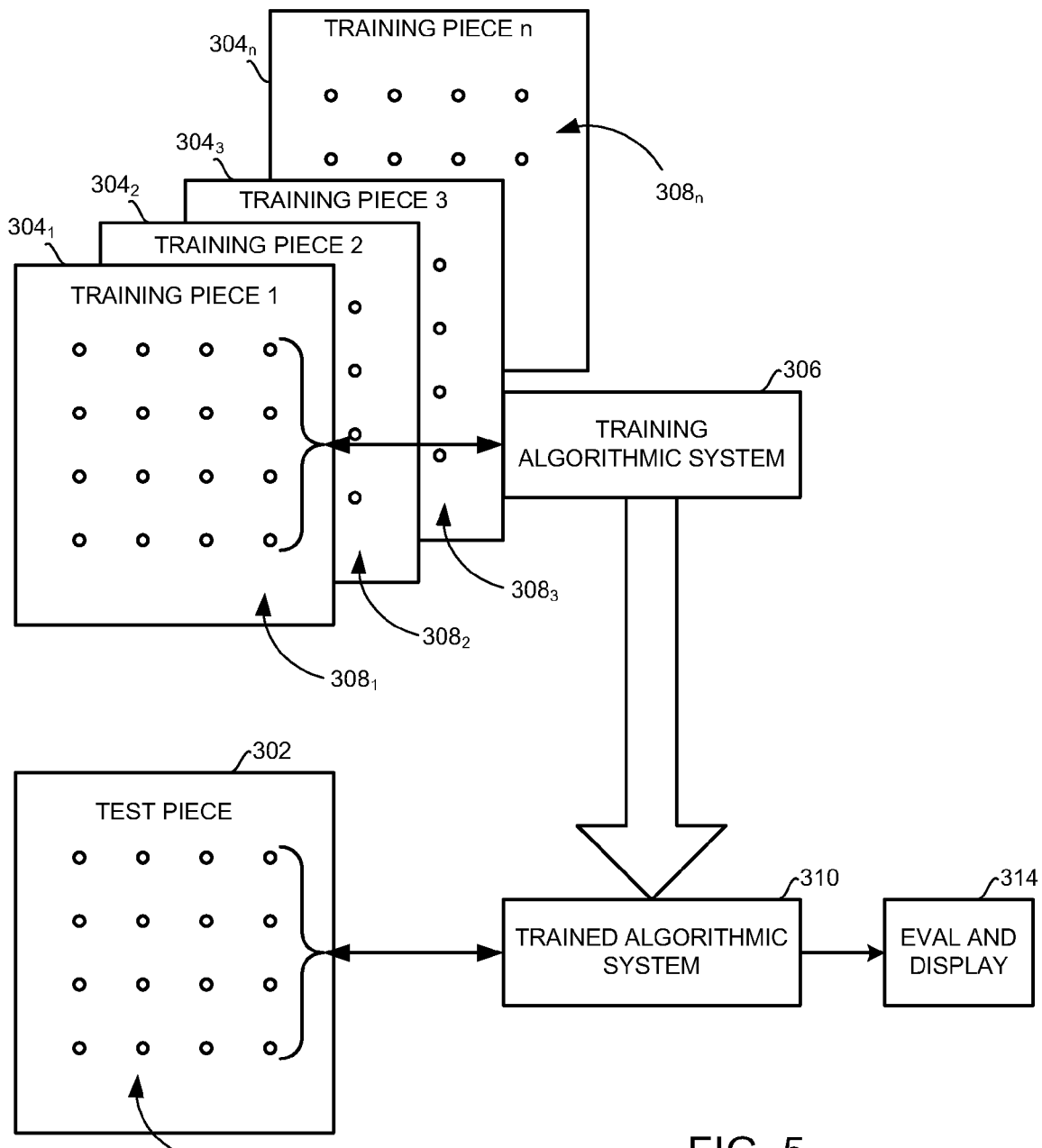
FIG. 5 is a schematic illustration of an embodiment of a system for evaluating structural features in a test piece for ascertaining presence of damage.

FIG. 5 is a schematic illustration of an embodiment of a system for evaluating structural features in a test piece for ascertaining presence of damage. In FIG. 5, a system 300 may include a test piece 302 in which structural changes may be evaluated for ascertaining presence of damage.

System 300 may also include at least one training piece $304_1$, $304_2$, $304_3$, $304_n$ substantially similar to test piece 302. The indicator "n" is employed to signify that there can be any number of training pieces in system 300. The inclusion of four training pieces $304_1$, $304_2$, $304_3$, $304_n$ in FIG. 5 is illustrative only and does not constitute any limitation regarding the number of training pieces that may be included in embodiments of the system of the present disclosure for evaluating structural changes in a test piece having damage.

System 300 may further include a training algorithmic system 306 coupled with at least one of training pieces $304_1$, $304_2$, $304_3$, $304_n$. System 300 may still further include a plurality of training transducer elements $308_n$ coupled with each training piece $304_n$. A plurality of transducer elements $308_1$ may be coupled with training piece $304_1$. A plurality of transducer elements $308_2$ may be coupled with training piece $304_2$. A plurality of transducer elements $308_3$ may be coupled with training piece $304_3$. A plurality of transducer elements $308_n$ may be coupled with training piece $304_n$. Pluralities of transducer elements $308_1$, $308_2$, $308_3$, $308_n$ may each be coupled with training algorithmic system 306. Connection of a respective plurality of transducer elements $308_n$ with training algorithmic system 306 may be effected in a serial manner so that only one respective plurality of transducer elements $308_n$ may be coupled and exercised with training algorithmic system 306 at a particular time.

A respective plurality of training transducer elements $308_n$ may be exercised by transmitting a plurality of training signals among the individual transducer elements of the respective plurality of training transducer elements $308_n$ after imposing damage to the training piece while the training algorithmic system processes information in the training signals relating to predetermined parameters relating to the evaluating. Weighted factors used by training algorithmic system 306 may be adjusted to reduce errors between results from training algorithmic system 306 and the predetermined parameters. The transmitting of training signals and adjusting of weighted factors may continue until errors are reduced to within predetermined limits.

System 300 may also include a trained algorithmic system 310 substantially similar to training algorithmic system 306. Trained algorithmic system 310 may be coupled with test piece 302 to process a plurality of test signals from a plurality of transducer elements 312. Plurality of transducer elements 312 may be substantially similar to a respective plurality of transducer elements $308_n$. Test signals from plurality of transducer elements 312 may be substantially similar to training signals from a respective plurality of transducer elements $308_n$. Trained algorithmic system 310 may employ test signals to effect evaluating structural features in test piece 302 for ascertaining presence of damage. The plurality of physical aspects may be less than ten physical aspects of the damage.

System 300 may further include an evaluation and display unit 314 coupled with trained algorithmic system 310 to effect an interface for use by a user (not shown in FIG. 5).

It is to be understood that, while the detailed drawings and specific examples given describe embodiments of the disclosure, they are for the purpose of illustration only, that the apparatus and method of embodiments of the disclosure are not limited to the precise details and conditions disclosed and that various changes may be made therein without departing from the spirit of the disclosure which is defined by the following claims:

We claim:

1. A method for quantifying damage in a test structure; said test structure having a plurality of transducer units coupled to at least one portion of said test structure; the method comprising:
    (a) training an evaluating algorithmic system coupled with said plurality of transducer units to establish a trained algorithmic system able to recognize a predetermined plurality of characteristics of signals traversing a plurality of paths through a training structure substantially similar to said test structure after said training structure is damaged; each respective path of said plurality of paths being situated between respective pairs of transducer units of said plurality of transducer units coupled to said training structure; said predetermined plurality of characteristics relating each said respective path of said plurality of paths to a plurality of physical aspects of said damage; and
    (b) employing said trained algorithmic system to recognize said predetermined plurality of characteristics of signals traversing a plurality of paths in said test structure to effect said quantifying; said plurality of physical aspects including less than ten physical aspects.

2. A method for quantifying damage in a test structure as recited in claim 1 wherein said test structure is a multi-layer member participating in enclosing a space; said test structure having an inside surface and an outside surface, and wherein said plurality of transducer units are coupled to one of said inside surface and said outside surface.

3. A method for quantifying damage in a test structure as recited in claim 1 wherein said signals are ultrasonic signals.

4. A method for quantifying damage in a test structure as recited in claim 1 wherein said trained algorithmic system is embodied in a nonlinear statistical data modeling and learned classification method.

5. A method for quantifying damage in a test structure as recited in claim 1 wherein said plurality of physical aspects includes at least two of a damage index, a distance from a respective said path to a center locus of said damage, a distance to said center locus from first transducer unit of a respective said pair of transducer units; a distance to said center locus from a second transducer unit of a respective said pair of transducer units; and a scatter angle associated with said damage and said respective pair of transducer units.

6. A method for quantifying damage in a test structure as recited in claim 2 wherein said plurality of physical aspects includes at least two of a damage index, a distance from a respective said path to a center locus of said damage, a distance to said center locus from first transducer unit of a respective said pair of transducer units; a distance to said center locus from a second transducer unit of a respective said pair of transducer units; and a scatter angle associated with said damage and said respective pair of transducer units.

7. A method for quantifying damage in a test structure as recited in claim 3 wherein said plurality of physical aspects includes at least two of a damage index, a distance from a respective said path to a center locus of said damage, a distance to said center locus from first transducer unit of a respective said pair of transducer units; a distance to said center locus from a second transducer unit of a respective said pair of transducer units; and a scatter angle associated with said damage and said respective pair of transducer units.

8. A method for quantifying damage in a test structure as recited in claim 4 wherein said plurality of physical aspects includes at least two of a damage index, a distance from a respective said path to a center locus of said damage, a distance to said center locus from first transducer unit of a respective said pair of transducer units; a distance to said center locus from a second transducer unit of a respective said pair of transducer units; and a scatter angle associated with said damage and said respective pair of transducer units.

9. A method for evaluating structural changes in a test piece having damage; the method comprising:
    (a) providing a training piece substantially similar to said test piece;
    (b) providing a training algorithmic system coupled with said training piece;
    (c) providing a plurality of training transducer elements coupled with said training piece and with said training algorithmic system;
    (d) exercising said plurality of training transducer elements by transmitting a plurality of training signals among said plurality of training transducer elements after imposing damage to said training piece while said training algorithmic system processes information in said training signals relating to predetermined parameters relating to said evaluating; said predetermined parameters relating to a plurality of physical aspects of said damage;
    (e) adjusting weighted factors used by said training algorithmic system to reduce errors between results from said training algorithmic system and said predetermined parameters;
    (f) repeating steps (d) and (e) until said errors are within predetermined limits; and
    (g) employing a trained algorithmic system substantially similar to said training algorithmic system coupled with said test piece to process a plurality of test signals similar to said training signals to effect said evaluating; said plurality of physical aspects being less than ten physical aspects of said damage.

10. A method for evaluating structural changes in a test piece having damage as recited in claim 9 wherein said test piece is a multi-layer member participating in enclosing a space; said test piece having an inside surface and an outside surface, and wherein said plurality of training transducer elements are coupled to one of said inside surface and said outside surface.

11. A method for evaluating structural changes in a test piece having damage as recited in claim 9 wherein said signals are ultrasonic signals.

12. A method for evaluating structural changes in a test piece having damage as recited in claim 9 wherein said trained algorithmic system is embodied in a nonlinear statistical data modeling and learned classification method.

13. A method for evaluating structural changes in a test piece having damage as recited in claim 9 wherein said plurality of physical aspects includes at least two of a damage index, a distance from a respective said path to a center locus of said damage, a distance to said center locus from first transducer unit of a respective said pair of transducer units; a distance to said center locus from a second transducer unit of a respective said pair of transducer units; and a scatter angle associated with said damage and said respective pair of transducer units.

14. A method for evaluating structural changes in a test piece having damage as recited in claim 10 wherein said plurality of physical aspects includes at least two of a damage index, a distance from a respective said path to a center locus of said damage, a distance to said center locus from first transducer unit of a respective said pair of transducer units; a distance to said center locus from a second transducer unit of a respective said pair of transducer units; and a scatter angle associated with said damage and said respective pair of transducer units.

15. A method for quantifying damage in a test structure as recited in claim 11 wherein said plurality of physical aspects includes at least two of a damage index, a distance from a respective said path to a center locus of said damage, a distance to said center locus from first transducer unit of a respective said pair of transducer units; a distance to said center locus from a second transducer unit of a respective said pair of transducer units; and a scatter angle associated with said damage and said respective pair of transducer units.

16. A method for quantifying damage in a test structure as recited in claim 12 wherein said plurality of physical aspects includes at least two of a damage index, a distance from a respective said path to a center locus of said damage, a distance to said center locus from first transducer unit of a respective said pair of transducer units; a distance to said center locus from a second transducer unit of a respective said pair of transducer units; and a scatter angle associated with said damage and said respective pair of transducer units.

17. A system for evaluating structural changes in a test piece having damage; the system comprising:
(a) a training piece substantially similar to said test piece;
(b) a training algorithmic system coupled with said training piece;
(c) a plurality of training transducer elements coupled with said training piece and
with said training algorithmic system; said plurality of training transducer elements being exercised by transmitting a plurality of training signals among said plurality of training transducer elements after imposing damage to said training piece; said training algorithmic system processing information in said training signals relating to predetermined parameters relating to said evaluating; adjusting weighted factors used by said training algorithmic system to reduce errors between results from said training algorithmic system and said predetermined parameters; said transmitting of training signals and adjusting of weighted factors continuing until said errors are reduced to within predetermined limits; said predetermined parameters relating to a plurality of physical aspects of said damage; and
(d) a trained algorithmic system substantially similar to said training algorithmic system coupled with said test piece to process a plurality of test signals similar to said training signals to effect said evaluating; said plurality of physical aspects being less than ten physical aspects of said damage.

18. A system for evaluating structural changes in a test piece having damage as recited in claim 17 wherein said signals are ultrasonic signals.

19. A system for evaluating structural changes in a test piece having damage as recited in claim 18 wherein said trained algorithmic system is embodied in a nonlinear statistical data modeling and learned classification method.

20. A system for evaluating structural changes in a test piece having damage as recited in claim 19 wherein said plurality of physical aspects includes at least two of a damage index, a distance from a respective said path to a center locus of said damage, a distance to said center locus from first transducer unit of a respective said pair of transducer units; a distance to said center locus from a second transducer unit of a respective said pair of transducer units; and a scatter angle associated with said damage and said respective pair of transducer units.

* * * * *